United States Patent
Verma et al.

(10) Patent No.: US 9,758,471 B2
(45) Date of Patent: Sep. 12, 2017

(54) PROCESS FOR THE PREPARATION OF 4-DIMETHYLAMINOCROTONIC ACID

(71) Applicant: SUN PHARMACEUTICAL INDUSTRIES LIMITED, Mumbai, Maharashtra (IN)

(72) Inventors: Shyam Sunder Verma, Benares (IN); Shravan Kumar Singh, Mirzapur (IN); Kaptan Singh, Gurgaon (IN); Mohan Prasad, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/315,880

(22) PCT Filed: Jun. 2, 2015

(86) PCT No.: PCT/IB2015/054177
§ 371 (c)(1),
(2) Date: Dec. 2, 2016

(87) PCT Pub. No.: WO2015/186065
PCT Pub. Date: Dec. 10, 2015

(65) Prior Publication Data
US 2017/0107172 A1    Apr. 20, 2017

(30) Foreign Application Priority Data

Jun. 2, 2014 (IN) .............. 1458/DEL/2014

(51) Int. Cl.
*C07C 227/18* (2006.01)
*C07D 239/94* (2006.01)

(52) U.S. Cl.
CPC .......... *C07C 227/18* (2013.01); *C07D 239/94* (2013.01)

(58) Field of Classification Search
CPC .............. C07D 239/94; C07C 227/18
See application file for complete search history.

(56) References Cited

U.S. PATENT DOCUMENTS

| | | | |
|---|---|---|---|
| 6,251,912 B1 | 6/2001 | Wissner et al. | 514/259 |
| 7,126,025 B2 | 10/2006 | Considine et al. | 562/868 |
| RE43,431 E | 5/2012 | Himmelsbach et al. | 514/266.22 |
| 2012/0046494 A1 | 2/2012 | Choi et al. | 562/574 |
| 2014/0018372 A1 | 1/2014 | Maier et al. | 514/256 |
| 2014/0051713 A1 | 2/2014 | Gidwani et al. | 514/266.24 |

FOREIGN PATENT DOCUMENTS

| | | | | |
|---|---|---|---|---|
| CN | 103755688 | * | 4/2014 | ........ C07D 405/12 |
| WO | WO 2013/052157 | | 4/2013 | ........ C07D 407/12 |

OTHER PUBLICATIONS

International Search Report and Written Opinion for International Application No. PCT/IB2015/054177, issued by PCT on Oct. 23, 2015.
International Preliminary Report on Patentability for International Application No. PCT/IB2015/054177, issued by PCT on Dec. 15, 2016.

\* cited by examiner

*Primary Examiner* — Erich A Leeser

(57) ABSTRACT

The present invention provides a process for the preparation of 4-dimethylaminocrotonic acid of Formula (II) or its salts, which is used as an intermediate for the preparation of afatinib or its salts.

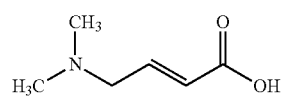

Formula II

15 Claims, No Drawings

PROCESS FOR THE PREPARATION OF 4-DIMETHYLAMINOCROTONIC ACID

FIELD OF THE INVENTION

The present invention provides a process for the preparation of 4-dimethylaminocrotonic acid of Formula II or its salts, which is used as an intermediate for the preparation of afatinib or its salts.

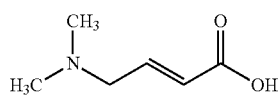

Formula II

BACKGROUND OF THE INVENTION

Afatinib is a tyrosine kinase inhibitor disclosed in U.S. Pat. Nos. RE43,431 and 6,251,912. Afatinib is depicted by Formula Ia:

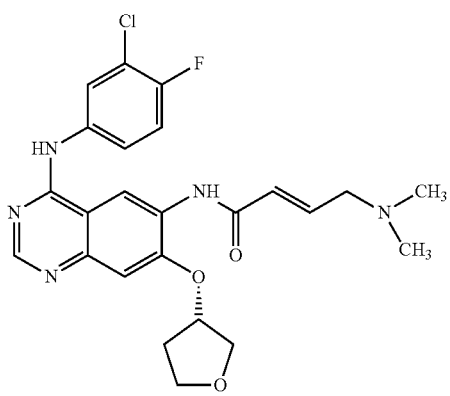

Formula Ia

Afatinib is presented as the dimaleate salt and is chemically designated as 2-butenamide, N-[4-[(3-chloro-4-fluorophenyl)amino]-7-[[(3S)-tetrahydro-3-furanyl]oxy]-6-quinazolinyl]-4-(dimethylamino)-,(2E)-,(2Z)-2-butenedioate (1:2) having the structure depicted by Formula I:

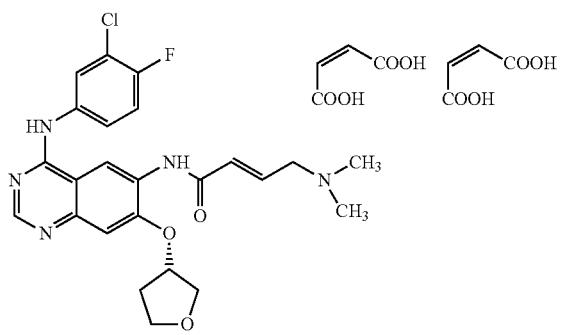

Formula I

Processes for the preparation of 4-dimethylaminocrotonic acid or its salts are disclosed in U.S. Pat. No. 7,126,025 and U.S. Publication No. 2012/0046494.

U.S. Pat. No. 7,126,025 discloses a process for the preparation of 4-dimethylaminocrotonic acid or its salts by reacting but-2-enoic acid with chlorotrimethylsilane in pyridine to obtain trimethylsilylcrotonate, which is brominated with a brominating agent under free radical conditions and in the presence of methylene chloride, acetonitrile, 1,2-dichloroethane, carbon tetrachloride, or ethyl acetate to give trimethylsilyl-4-bromocrotonate. The bromocrotonate compound is treated with dimethylamine in tetrahydrofuran to provide the 4-dimethylaminocrotonic acid.

U.S. Pat. No. 7,126,025 also discloses a process for the preparation of 4-dimethylaminocrotonic acid by treating methyl or ethyl 4-bromocrotonate with dimethylamine to provide methyl or ethyl 4-dimethylaminocrotonate, which is hydrolyzed to provide the 4-dimethylaminocrotonic acid.

U.S. Publication No. 2012/0046494 discloses a process for the preparation of 4-dimethylaminocrotonic acid or its salts by converting alkyl 4-chloro-3-hydroxy butyrate to alkyl 4-hydroxy crotonate, which is brominated to obtain alkyl 4-bromo crotonate. The alkyl 4-bromo crotonate is treated with dimethyl amine to provide alkyl 4-dimethylaminocrotonate, which is hydrolyzed to get the 4-dimethylaminocrotonic acid.

The use of pyridine or carbon tetrachloride is toxic to humans and therefore their use for the manufacture of a drug substance is not advisable. The bromocrotonate compounds, being lachrymatory in nature, are difficult to handle on an industrial scale.

The present invention provides a faster, more efficient, and industrially feasible process for the preparation of 4-dimethylaminocrotonic acid of Formula II, which is used as an intermediate for the preparation of afatinib or its salts.

SUMMARY OF THE INVENTION

A first aspect of the present invention provides a process for the preparation of 4-dimethylaminocrotonic acid of Formula II or its salts,

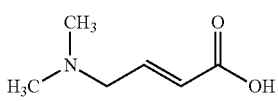

Formula II comprising the steps of:
i) converting 2,2-diethoxy-N,N-dimethylethanamine of Formula III

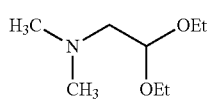

Formula III to ethyl-4-(dimethylamino)crotonate of Formula IV; and

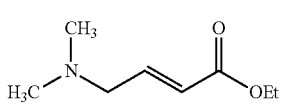

Formula IV ii) hydrolyzing the ethyl-4-(dimethylamino)crotonate of Formula IV.

A second aspect of the present invention provides a process for the preparation of afatinib of Formula Ia or its salts,

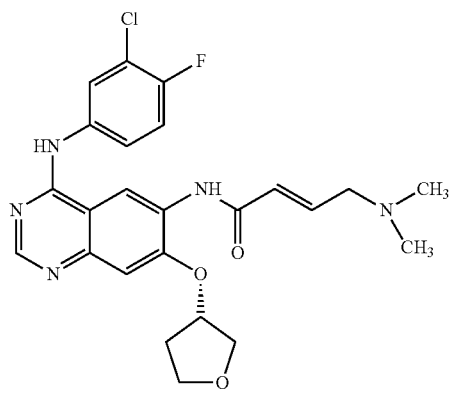

Formula Ia comprising the steps of:
i) converting 2,2-diethoxy-N,N-dimethylethanamine of Formula III

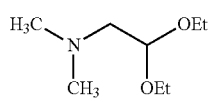

Formula III to ethyl-4-(dimethylamino)crotonate of Formula IV;

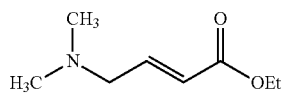

Formula IV ii) hydrolyzing the ethyl-4-(dimethylamino)crotonate of Formula IV to obtain 4-dimethylaminocrotonic acid of Formula II or its salts; and

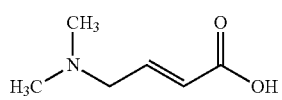

Formula II iii) converting the 4-dimethylaminocrotonic acid of Formula II or its salts to afatinib of Formula Ia or its salts.

DETAILED DESCRIPTION OF THE INVENTION

Various embodiments and variants of the present invention are described hereinafter.

The term "about," as used herein, refers to any value which lies within the range defined by a number up to ±10% of the value.

The term "salts," as used herein, refers to an acid addition salt of a compound, wherein the acid can be selected from inorganic acids and organic acids. Examples of inorganic acids include hydrochloric acid, hydrobromic acid, or the like. Examples of organic acids include formic acid, acetic acid, lactic acid, malonic acid, citric acid, quinic acid, succinic acid, oxalic acid, maleic acid, tartaric acid, fumaric acid, camphor sulfonic acid, and the like.

The conversion of 2,2-diethoxy-N,N-dimethylethanamine of Formula III to ethyl-4-(dimethylamino)crotonate of Formula IV is carried out in the presence of an acid to provide (dimethylamino)acetaldehyde in-situ, followed by its treatment with ethyl (diethoxyphosphoryl)acetate in the presence of a base and a solvent.

The acid to be used for the in-situ generation of (dimethylamino)acetaldehyde can be selected from sulphuric acid, hydrochloric acid, nitric acid, and mixtures thereof. A preferred acid is hydrochloric acid.

The base to be used for the reaction (dimethylamino)acetaldehyde with ethyl (diethoxyphosphoryl)acetate to produce ethyl-4-(dimethylamino)crotonate of Formula IV can be selected from sodium hydroxide, potassium hydroxide, sodium bicarbonate, potassium bicarbonate, and mixtures thereof. A preferred base is potassium hydroxide.

The solvent to be used for the reaction (dimethylamino)acetaldehyde with ethyl (diethoxyphosphoryl)acetate to produce ethyl-4-(dimethylamino)crotonate of Formula IV can be selected from 2-methyltetrahydrofuran, diethyl ether, ethyl tert-butyl ether, and mixtures thereof. A preferred solvent is 2-methyltetrahydrofuran.

The hydrolysis of ethyl-4-(dimethylamino)crotonate of Formula IV to 4-dimethylaminocrotonic acid of Formula II or its salts is carried out in the presence of a base or an acid, and a solvent.

The base to be used for the hydrolysis can be selected from sodium hydroxide, potassium hydroxide, sodium bicarbonate, potassium bicarbonate, and mixtures thereof. The acid to be used for the hydrolysis can be selected from sulphuric acid, hydrochloric acid, nitric acid, and mixtures thereof. A preferred base is sodium hydroxide; a preferred acid is hydrochloric acid.

The solvent to be used for the hydrolysis can be selected from water, methanol, ethanol, n-propanol, isopropanol, butanol, or mixtures thereof.

The conversion of 4-dimethylaminocrotonic acid of Formula II or its salts to afatinib of Formula Ia or its salts can be carried out by processes known in the art, such as those disclosed in U.S. Publication No. 2012/0046494.

In the foregoing section, embodiments are described by way of examples to illustrate the process of the present invention. However, these are not intended in any way to limit the scope of the present invention. Several variants of these examples would be evident to persons ordinarily skilled in the art which are within the scope of the present invention.

EXAMPLES

Example 1: Preparation of ethyl-4-(dimethylamino)crotonate (Formula IV)

In a round bottom flask, 2,2-diethoxy-N,N-dimethylethanamine (Formula III, 200 g) and deionized water (100 mL) were added at about 20° C. to about 25° C. To the solution, concentrated hydrochloric acid (240 mL) was added at about 25° C. to about 50° C. The temperature of the reaction mixture was raised to about 70° C. The reaction mixture was stirred at about 60° C. to about 70° C. for about 12 hours. The reaction mixture was cooled to about 0° C. To the reaction mixture, about 200 mL of aqueous potassium hydroxide (240 g in 250 mL water) was added at about 0° C. to about 10° C. to attain a pH of 9.0. To the reaction mixture, ethyl(diethoxyphosphoryl) acetate (200 g) and 2-methyltetrahydrofuran (600 mL) were added at about 0° C. to about 5° C. Further, 50 mL of aqueous potassium hydroxide was added to the reaction mixture at about −5° C. to about 0° C. to attain a pH of about 13.5. The reaction mixture was stirred at about −5° C. to about 0° C. for about 1 hour. The reaction mixture was filtered, and then the filtrate was recovered under vacuum at about 45° C. to about 50° C. to obtain ethyl-4-(dimethylamino)crotonate as an oily mass.
Yield: 89%

Example 2: Preparation of 4-dimethylaminocrotonic acid hydrochloride (Formula II)

In a round bottom flask, ethyl-4-(dimethylamino)crotonate (Formula IV, 120 g) and ethanol (480 mL) were added at about 25° C. to about 35° C. To the solution, aqueous sodium hydroxide (30.5 g in 60 mL water) was added at about 10° C. to about 20° C. The temperature of the reaction mixture was raised to about 50° C. The reaction mixture was stirred at about 50° C. to about 55° C. for about 1 hour. The reaction mixture was cooled to about 5° C. To the reaction mixture, concentrated hydrochloric acid (120 mL) was added to attain a pH of 1.5. The reaction mixture was filtered on Celite® and washed with ethanol (50 mL). The filtrate was recovered under vacuum at about 55° C. to about 60° C. to obtain a crude mass. Ethanol (240 mL) was added to the crude mass, and then the reaction mixture was stirred at about 55° C. to about 60° C. for about 15 minutes to obtain a solution. In the solution, sodium chloride was obtained as a byproduct. The solution was filtered to discard sodium chloride. The filtrate was recovered under vacuum at about 55° C. to about 60° C. to obtain a residue. To the residue, isopropanol (400 mL) was added, and then the reaction mixture was stirred at about 55° C. to about 60° C. to obtain a clear solution. The solution was gradually cooled to about 25° C. to about 30° C. The solution was further stirred at the same temperature for about 2 hours. The solid obtained was filtered, and then washed with isopropanol (50 mL). The solid was dried under vacuum at about 55° C. to about 60° C. to provide 4-dimethylaminocrotonic acid hydrochloride.
Yield: 63%

We claim:
1. A process for the preparation of 4-dimethylaminocrotonic acid of Formula II or its salts,

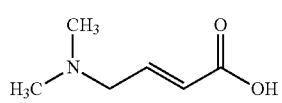

Formula II comprising the steps of:
  i) converting 2,2-diethoxy-N,N-dimethylethanamine of Formula III

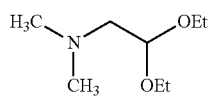

Formula III to ethyl-4-(dimethylamino)crotonate of Formula IV; and

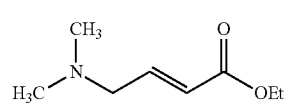

Formula IV ii) hydrolyzing the ethyl-4-(dimethylamino)crotonate of Formula IV.
2. The process according to claim 1 further comprising converting the 4-dimethylaminocrotonic acid of Formula II or its salts to afatinib of Formula Ia or its salts,

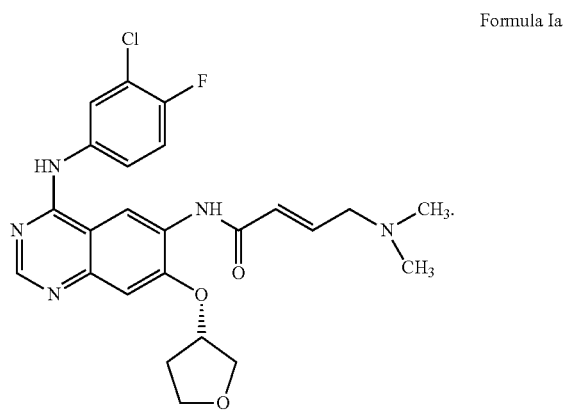

Formula Ia

3. The process according to claim 1, wherein the conversion of the 2,2-diethoxy-N,N-dimethylethanamine of Formula III to the ethyl-4-(dimethylamino)crotonate of Formula IV is carried out in the presence of an acid to provide (dimethylamino)acetaldehyde in-situ, followed by its treatment with ethyl (diethoxyphosphoryl)acetate in the presence of a base and a solvent.
4. The process according to claim 3, wherein the acid is selected from sulphuric acid, hydrochloric acid, nitric acid, or mixtures thereof.
5. The process according to claim 3, wherein the acid is hydrochloric acid.
6. The process according to claim 3, wherein the base is selected from the group consisting of sodium hydroxide, potassium hydroxide, sodium bicarbonate, potassium bicarbonate, or mixtures thereof.
7. The process according to claim 3, wherein the base is potassium hydroxide.
8. The process according to claim 3, wherein the solvent is selected from the group consisting of 2-methyltetrahydrofuran, diethyl ether, ethyl tert-butyl ether, or mixtures thereof.
9. The process according to claim 3, wherein the solvent is 2-methyltetrahydrofuran.
10. The process according to claim 1, wherein the hydrolysis of the ethyl-4-(dimethylamino)crotonate of Formula IV to the 4-dimethylaminocrotonic acid of Formula II or its salts is carried out in the presence of a base or an acid, and a solvent.
11. The process according to claim 10, wherein the base is selected from the group consisting of sodium hydroxide, potassium hydroxide, sodium bicarbonate, potassium bicarbonate or mixtures thereof.

12. The process according to claim 10, wherein the base is sodium hydroxide.

13. The process according to claim 10, wherein the acid is selected from the group consisting of sulphuric acid, hydrochloric acid, nitric acid, or mixtures thereof.

14. The process according to claim 10, wherein the acid is hydrochloric acid.

15. The process according to claim 10, wherein the solvent is selected from the group consisting of water, methanol, ethanol, n-propanol, isopropanol, butanol, or mixtures thereof.

* * * * *